United States Patent
Prater et al.

(10) Patent No.: US 12,399,117 B2
(45) Date of Patent: Aug. 26, 2025

(54) WIDE AREA OPTICAL PHOTOTHERMAL INFRARED SPECTROSCOPY

(71) Applicant: Photothermal Spectroscopy Corp., Santa Barbara, CA (US)

(72) Inventors: Craig Prater, Santa Barbara, CA (US); Derek Decker, Santa Barbara, CA (US); Roshan Shetty, Westlake Village, CA (US)

(73) Assignee: Photothermal Spectroscopy Corp., Santa Barbara, CA (US)

( * ) Notice: Subject to any disclaimer, the term of this patent is extended or adjusted under 35 U.S.C. 154(b) by 0 days.

(21) Appl. No.: 18/385,233

(22) Filed: Oct. 30, 2023

(65) Prior Publication Data
US 2024/0060885 A1    Feb. 22, 2024

Related U.S. Application Data

(63) Continuation of application No. 17/250,124, filed as application No. PCT/US2019/034944 on May 31, 2019, now Pat. No. 11,879,837.
(Continued)

(51) Int. Cl.
*G01N 21/3563* (2014.01)
*C12M 1/00* (2006.01)
(Continued)

(52) U.S. Cl.
CPC ......... *G01N 21/3563* (2013.01); *C12M 21/02* (2013.01); *C12M 29/00* (2013.01);
(Continued)

(58) Field of Classification Search
CPC ......... G01N 21/3563; G01N 2201/061; G01N 2201/062; G01N 2021/1725; G01N 21/171; C12M 21/02; C12M 29/00; C12M 29/04; C12M 29/22; C12M 33/00; C12M 39/00; C12M 41/12; C12M 41/26; C12M 41/34;
(Continued)

(56) References Cited

U.S. PATENT DOCUMENTS

| 9,091,594 B2 | 7/2015 | Furstenberg |
| 11,879,837 B2 | 1/2024 | Prater |

(Continued)

FOREIGN PATENT DOCUMENTS

| JP | 2003-042713 A | 2/2003 |
| JP | 2004286577 A | 10/2004 |

(Continued)

OTHER PUBLICATIONS

Japanese Office Action, Application No. 2020-566811, dated Oct. 31, 2023, 5 pages (10 pages with translation).
(Continued)

*Primary Examiner* — Kiho Kim
(74) *Attorney, Agent, or Firm* — MERCHANT & GOULD P.C.

(57) ABSTRACT

Apparatuses and methods for microscopic analysis of a sample by simultaneously characterizing infrared absorption characteristics of a plurality of spatially resolved locations are described herein. These apparatuses and methods improve sampling times while collecting microscopic data regarding composition of a sample across a wide field.

29 Claims, 10 Drawing Sheets

Related U.S. Application Data

(60) Provisional application No. 62/679,588, filed on Jun. 1, 2018.

(51) Int. Cl.

| | | |
|---|---|---|
| C12M 1/26 | (2006.01) | |
| C12M 1/34 | (2006.01) | |
| C12M 1/36 | (2006.01) | |
| C12N 1/12 | (2006.01) | |
| G02B 21/06 | (2006.01) | |
| G02B 21/36 | (2006.01) | |
| G06T 7/00 | (2017.01) | |
| H04N 23/74 | (2023.01) | |
| H04N 23/741 | (2023.01) | |

(52) U.S. Cl.
CPC ............ *C12M 29/04* (2013.01); *C12M 29/22* (2013.01); *C12M 33/00* (2013.01); *C12M 39/00* (2013.01); *C12M 41/12* (2013.01); *C12M 41/26* (2013.01); *C12M 41/34* (2013.01); *C12M 41/36* (2013.01); *C12M 41/44* (2013.01); *C12M 41/48* (2013.01); *C12N 1/12* (2013.01); *G02B 21/06* (2013.01); *G02B 21/365* (2013.01); *G06T 7/97* (2017.01); *H04N 23/74* (2023.01); *H04N 23/741* (2023.01); *G01N 2201/061* (2013.01); *G01N 2201/062* (2013.01); *G06T 2207/10048* (2013.01); *G06T 2207/10056* (2013.01); *G06T 2207/10152* (2013.01)

(58) Field of Classification Search
CPC ...... C12M 41/36; C12M 41/44; C12M 41/48; C12N 1/12; G02B 21/06; G02B 21/365; G02B 21/002; G02B 21/082; G02B 21/12; G02B 21/16; G06T 7/97; G06T 2207/10048; G06T 2207/10056; G06T 2207/10152; H04N 23/74; H04N 23/741
See application file for complete search history.

(56) References Cited

U.S. PATENT DOCUMENTS

| | | | |
|---|---|---|---|
| 2002/0167724 | A1 | 11/2002 | Iketaki |
| 2004/0085540 | A1 | 5/2004 | Lapotko |
| 2004/0188602 | A1 | 9/2004 | Chinn |
| 2008/0151239 | A1 | 6/2008 | Iketaki |
| 2010/0302537 | A1 | 12/2010 | Chauchard |
| 2013/0134310 | A1* | 5/2013 | Furstenberg ............ G01J 3/443 250/353 |
| 2014/0055784 | A1 | 2/2014 | Kremer |
| 2017/0211977 | A1* | 7/2017 | Jeys ........................ G01J 3/433 |
| 2018/0088041 | A1 | 3/2018 | Zhang |
| 2018/0120344 | A1 | 5/2018 | Prater |
| 2018/0246032 | A1 | 8/2018 | Li |

FOREIGN PATENT DOCUMENTS

| | | | |
|---|---|---|---|
| JP | 2006242862 | A | 9/2006 |
| JP | 2008-157873 | A | 7/2008 |
| JP | 2012-519836 | A | 8/2012 |
| WO | 2018073169 | A1 | 4/2018 |
| WO | 2019232399 | A1 | 12/2019 |

OTHER PUBLICATIONS

Journal of Japan Society of Colour Material vol./Article 86, Issue 6 (Jun. 20, 2013) pp. 225-230.
Wang et al., "Thermoreflectance Imaging of Optically Pumped Gap Plasm on Structures," 2018 Conference on Lasers and Electro-Optics (CLEO), OSA, May 13, 2018, pp. 1-2.
Yazawa et al., "Optical Pump-Probe Thermoreflectance Imaging for Anisotropic Heat Diffusion," 2018 17th IEEE Intersociety Conference on Thermal and Thermomechanical Phenomena in Electronic Systems (THERM), IEEE, May 29, 2018, pp. 59-66.
EP Application No. 19811466.2, Extended European Search Report dated Feb. 2, 2022, 11 pages.
International Preliminary Report on Patentability from PCT Application PCT/US2019/034944, dated Jul. 31, 2020, 19 pgs.
International Search Report and Written Opinion PCT Application PCT/US2019/034944, dated Aug. 22, 2019, 8 pgs.
Grainger, Infrared Visual Thermometer, available at https://www.grainger.com/product/32MX58cm mmc=PPC:+Google+PLA s kwcid=AL29663 50916685317 g3 1 1839354215 ef _id=WsNtgAABDBgeinn:20180529203910:s, accessed Dec. 1, 2020, 3 pgs.
Stoly Arov, et al. "Photothermal speckle modulation for noncontact materials characterization", Optics Letters, vol. 40, No. 24, Dec. 15, 2015, 4 pgs.
Sullenberger, et al., "Spatially-resolved individual particle spectroscopy using photothermal modulation of Mie scattering", Optics Letters, vol. 42, No. 2, Jan. 15, 2017, 4 pgs.
Tamamitsu, et al., "Quantitative phase imaging with molecular vibrational sensitivity", Optics Letters, vol. 44, No. 15, Aug. 1, 2019, 4 pgs.
Unknown, "Chapter 1 Photothermal Lens Technique—Theory and Instrumentation", Date unknown, viewed Dec. 1, 2020, 42 pgs.
Boyer, et al., "Photothermal Imaging of Nanometer-Sized Metal Particles Among Scatterers", Downloaded from www.sciencemag.org on Feb. 9, 2009, 6 pgs.
Gadiuk, et al., "Room-Temperature Detection of a Single Molecules Absorption by Photothermal Contrast", Science, vol. 330, Oct. 15, 2010, 5 pgs.
Gadiuk, et al., "Supporting Online Material for Room-Temperature Detection of a Single Molecules Absorption by Photothermal Contrast", Science, vol. 330, Oct. 15, 2010, 14 pgs.
Fournier, et al., "Tomographic Approach for Photothermal Imaging Using the Mirage Effect", Journal de Physique Colloques, 44 (C6), 1983, 5 pgs.
Furstenberg, et al., Chemical Imaging using Infrared Photothermal Microspectroscopy, Next-Generation Spectroscopic Technologies V, Proc. of SPIE vol. 8374, 2012, 10 pgs.
Mertiri, et al., "Nonlinear Midinfrared Photothermal Spectroscopy Using Zharov Splitting and Quantum Cascade Lasers", ACS Publications, Jul. 18, 2014, 7 pgs.
Mertiri, et al., "Mid-infrared Photothermal heterodyne spectroscopy in a liquid crystal using a quantum cascade laser", Applied Physics Letters, 101, Jul. 23, 2012, 4 pgs.
Lasne, et al., "Label-free optical imaging of mitochondria in live cells", Optics Expres, vol. 15, No. 21, Oct. 17, 2007, 10 pgs.
Li, et al., "Super-resolution imaging with mid-IR Photothermal microscopy on the single particle level", Physical Chemistry ofInterfaces and Nanomaterials XIV, Proc. of SPIE vol. 9549, 2015, 8 pgs.
Mertiri, et al., "Label Free Mid-IR Photothermal Imaging of Bird Brain With Quantum Cascade Laser", CLEO, 2014, 2 pgs.
Harada, et al., "Photothermal Microscopy with Excitation and Probe Beams Coaxial under the Microscope and Its Application to Microparticle Analysis," Anal. Chem, 1993, 65, 3 pgs.
Li, et al., "Super-resolution Mid-infrared Imaging using Photothermal Microscopy", CLEO, 2016, 2 pgs.
Li, et al., "Super-Resolution Far-Field Infrared Imaging by Photothermal Heterodyne Imaging", Journal of Physical Chemistry, Jul. 25, 2017, 9 pgs.
Zhang, et al., "Depth-resolved mid-infrared Photothermal imaging of living cells and organisms with submicrometer spatial resolution", Sci. Adv., 2016 8 pgs.
Cariou, et al., Refractive-index variations with temperature of PMMA and polycarbonate, Applied Optics, vol. 25, No. 3, Feb. 1, 1986, 3 pgs.
Li, et al., "Mid-infrared Photothermal Imaging of Active Pharmaceutical Ingredients at Submicrometer Spatial Resolution", Unknown date, viewed Dec. 1, 2020, 5 pgs.
Sander, "Mid-Infrared Photothermal Imaging", Frontiers in Optics/Laser Science, 2015, 1 pg.

(56) References Cited

OTHER PUBLICATIONS

Japanese Office Action dated Feb. 25, 2025, Japanese Application No. 2020-566811, filing date Nov. 24, 2020, 13 pages, with English translation.
Japanese Application No. 2020-566811, filed May 31, 2019, Decision of Rejection, mailing date Jun. 3, 2025, 10 pages.

* cited by examiner

WIDE AREA OPTICAL PHOTOTHERMAL INFRARED SPECTROSCOPY

PRIORITY

This application is a continuation of U.S. patent application Ser. No. 17/250,124, filed Dec. 1, 2020, which is a National Phase entry of PCT Application No. PCT/US2019/034944, filed May 31, 2019, which claims priority to U.S. Provisional Application No. 62/679,588 filed Jun. 1, 2018, the disclosure of which is hereby incorporated by reference.

TECHNICAL FIELD

This disclosure relates to investigating or analyzing materials by the use of optical means, i.e. using infra-red, visible or ultra-violet light.

BACKGROUND

This disclosure is related to infrared spectroscopy and imaging with spatial resolution down to the sub-micron scale using an optical photothermal detection technique. Some optical photothermal techniques have been described in U.S. Pat. Nos. 9,091,594 and 9,841,324, for example. These references often refer to the technique by different names and acronyms. For the purposes of this application, we will refer to these techniques collectively and, in this application, as Optical Photothermal Infrared (OPTIR).

Several research groups have worked in this general field of OPTIR, including researchers at Naval Research Laboratory, Purdue University, Notre Dame University, Boston University, and the Massachusetts Institute of Technology. Instruments developed in these labs use visible light beams to probe the photothermal response of samples in response to absorption of infrared radiation. Potentially relevant background publications and patents include: (1) R. Furstenberg, C. Kendziora, N. D. Bassim, R. A. McGill, and V. K. Nguyen, U.S. Pat. No. 9,091,594 B2 (2015); (2) C. Li, D. Zhang, M. N. Slipchenko, and J.-X. Cheng, Anal. Chem., 89, 9, 4863-4867 (2017); (3) D. Zhang, C. Li, C. Zhang, M. N. Slipchenko, G. Eakins, and J.-X. Cheng, Science Advances, 2, 9, e1600521 (2016). (4) Z. Li, K. Aleshire, M. Kuno, and G. V. Hartland, The Journal of Physical Chemistry B, 121, 37, 8838-8846 (2017); (5) Z. Li, M. Kuno, and G. Hartland, "Super-resolution imaging with mid-IR photothermal microscopy on the single particle level", in SPIE Nanoscience+ Engineering (International Society for Optics and Photonics, 2015), p. 954912-954912-954918; (6) Z. Li, M. Kuno, and G. Hartland, "Super-resolution Mid-infrared Imaging using Photothermal Microscopy", in Conference on Lasers and Electro-Optics (Optical Society of America, San Jose, California, 2016), p. ATu3J.7; (7) A. Mërtiri, A. Totachawattana, H. Liu, M. K. Hong, T. Gardner, M. Y. Sander, and S. Erramilli, "Label free mid-IR photothermal imaging of bird brain with quantum cascade laser", in CLEO: Applications and Technology (Optical Society of America, 2014), p. AF1B. 4; (8) M. Y. Sander, "Mid-infrared photothermal imaging", in Laser Science (Optical Society of America, 2015), p. LM1I. 2; (9) U.S. Pat. No. 9,091,594 B2, entitled "Chemical mapping using thermal microscopy at the micro and nano scales," assigned to the U.S. Secretary of Navy.

There are also devices that have been constructed using off axis illumination and camera sensors to detect photothermal modulation of laser speckle, as discussed, for example, in A. M. Stolyarov, R. M. Sullenberger, D. R. Crompton, T. H. Jeys, B. G. Saar, and W. D. Herzog, Opt. Lett., 40, 24, 5786-5789 (2015), as well as variations in light scattering, as discussed, for example, in R. M. Sullenberger, S. M. Redmond, D. Crompton, A. M. Stolyarov, and W. D. Herzog, Opt. Lett., 42, 2, 203-206 (2017). These approaches, however, are not suitable for microscopy applications for sub-micron dimensions because of focal length/numerical aperture limitations placed on sample imaging optics.

A key limitation in the prior art of photothermal imaging and spectroscopy is that the photothermal effect due to IR absorption can be quite small. For example, the total intensity modulation in collected probe light due to absorption of IR radiation by the sample can be three to six orders of magnitude less than the average intensity of the total collected probe light. Because of this, it can be a challenge to detect small absorptions of IR radiation, either from weakly absorbing samples, samples with weak photothermal responses, and/or microscopically small amounts of sample material. Increasing the measurement time to accomplish orders of magnitude increases in precision is often not practicable. Measurement precision increases proportional to the square root of the sampling time, however, and so increasing the precision of an OPTIR detector by increasing sampling time is limited as a practical matter because achieving, for example, one order of magnitude improvement in precision requires sampling times to be increased by a factor of 100.

SUMMARY

According to embodiments described herein, an apparatus is provided for microscopic analysis of a sample by simultaneously characterizing infrared absorption characteristics of a plurality of spatially resolved locations. The plurality of spatially resolved locations correspond to a wide area of the sample. The apparatus includes a source of infrared radiation configured to illuminate the wide area of the sample with a beam of infrared radiation, a source of probe radiation configured to illuminate the wide area of the sample with a beam of probe radiation, a collector configured to collect as collected probe radiation at least a portion of probe radiation from each of the plurality of spatially resolved locations on the sample, and at least one camera configured to detect at least a portion of the collected probe radiation to generate signals indicative of infrared absorption corresponding to each one of the plurality of spatially resolved locations.

This application is related to novel instruments and methods that improve the measurement throughput via measurements of IR absorption on the microscopic scale for sub-micron dimensions conducted simultaneously over a wide area of a sample. The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
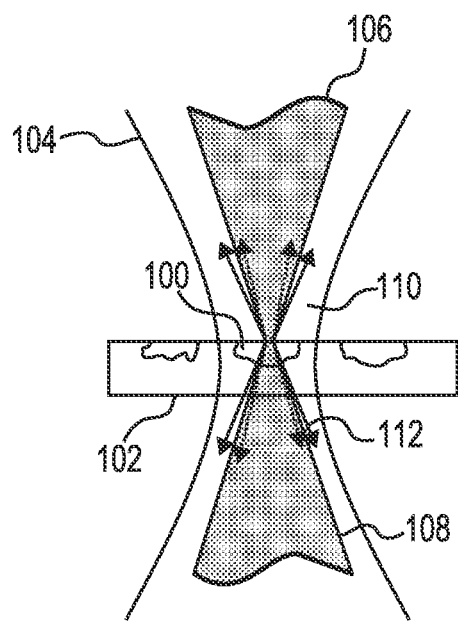
FIG. 1 shows a simplified schematic diagram of the photothermal principle employed by optical photothermal infrared (OPTIR) spectroscopy and imaging.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

This specification described methods and apparatuses for performing optical photothermal infrared (OPTIR) imaging and spectroscopy with improved sensitivity, improved signal-to-noise ratio, and decreased background signal. By using wide area techniques, parallel measurements can be made simultaneously to improve scanning speed and accuracy.

Several definitions are provided below for phrases that are used throughout the application.

"Illuminating" means to direct radiation at an object, for example a surface of a sample. Illumination may include any arbitrary configuration of radiation sources, pulse generators, modulator, reflecting elements, focusing elements and any other beam steering or conditioning elements.

In the context of light interacting with a sample, the word "interacting" means that light illuminating a sample is at least one of scattered, refracted, absorbed, aberrated, diverted, diffracted, transmitted, and reflected by, through and/or from the sample.

"Infrared source" and "source of infrared radiation" refer to one or more optical sources that generates or emits radiation in the infrared wavelength range, generally between 2-25 microns. The radiation source may be one of a large number of sources, including thermal or Globar sources, supercontinuum laser sources, frequency combs, difference frequency generators, sum frequency generators, harmonic generators, optical parametric oscillators (OPOs), optical parametric generators (OPGs), quantum cascade lasers (QCLs), nanosecond, picosecond, femtosecond and attosecond laser systems, CO2 lasers, microscopic heaters, and/or any other source that produces a beam of radiation. The source emits infrared radiation in a preferred embodiment, but it can instead or also emit in other wavelength ranges, for example from ultraviolet to THz. The source may be narrowband, for example with a spectral width of <10 $cm^{-1}$ or <1 $cm^{-1}$ less, or may be broadband, for example with a spectral width of >10 $cm^{-1}$, >100 $cm^{-1}$ or greater than 500 $cm^{-1}$.

"Probe beam" is a beam of light that is focused onto a sample to detect a photothermal distortion or other optical distortion resulting from the interaction of IR radiation with the sample, for example to detect the absorption of IR radiation by the sample.

"Source of probe radiation" refers to a radiation source that produces a probe beam. The Source of probe radiation will generally produce a probe beam comprising one or more emission wavelengths generally within the wavelength range from the visible to ultraviolet, but it may also or instead generate radiation at shorter or longer wavelengths, for example in the near-IR, extreme-UV or even x-ray range. The source of probe radiation may comprise a gas laser, a laser diode, a diode pumped solid state laser, a superluminescent diode (SLD), a UV and/or visible laser beam generated via sum frequency or difference frequency generation, for example, or any other source of laser or other coherent radiation. It may also comprise an incoherent source, for example an incandescent source, a light emitting diode or other light source. In a one embodiment it may also comprise any or other sources of UV and/or visible light that can be focused to a spot on the scale smaller than 2.5 micrometer, and preferably smaller than 1 micrometer.

"Spectrum" refers to a measurement of one or more properties of a sample as a function of wavelength or equivalently (and more commonly) as a function of wavenumber.

"Optical property" refers to an optical property of a sample, including but not limited to index of refraction, absorption coefficient, reflectivity, absorptivity, scattering, real and/or imaginary components of the index refraction, real and/or imaginary components of the sample dielectric function and/or any property that is mathematically derivable from one or more of these optical properties.

"Optical response" refers to the result of interaction of radiation with a sample. The optical response is related to one or more optical properties defined above. The optical response can be an absorption of radiation, a temperature increase, a thermal expansion, a photo-induced force, the reflection and/or scattering of light or other response of a material due to the interaction with illuminating radiation.

"Signal indicative of refers to a signal that is mathematically related to a property of interest. The signal may be an analog signal, a digital signal, and/or one or more numbers stored in a computer or other digital electronics." The signal may be a voltage, a current, or any other signal that may be readily transduced and recorded. The signal may be mathematically identical to the property being measured, for example explicitly an absolute phase signal or an absorption coefficient. It may also be a signal that is mathematically related to one or more properties of interest, for example including linear or other scaling, offsets, inversion, or even complex mathematical manipulations.

A "scanner" is one or more scanning mechanisms used to generate relative translation between the probe and the sample so that the probe can interact with and measure properties of a plurality of positions on a sample. The scanning mechanism can move either the probe, the sample or a combination thereof. The scanning mechanisms are usually piezoelectric devices, but can also employ other mechanisms like electromagnetic, electrostatic, electrostictive and other drive mechanisms that induce a desired motion in response to a given control signal or command. Scanners include, but are not limited to piezoelectric tubes, piezoelectric stacks, piezoelectric driven flexure stages, voice coils, and other mechanisms for providing precision translation.

A "controller" refers to a system to facilitate data acquisition and control of the system.

The controller may be a single integrated electronic enclosure or may comprise multiple distributed elements. The control elements may provide control for positioning and/or scanning of the probe, illumination and/or sample. They may also collect data about the probe modulation, profile motion or other response, provide control over the radiation source power, polarization, modulation, steering, focus and/or other functions. The control elements may include a computer program method or a digital logic method and may be implemented using any combination of a variety of computing devices (computers, Personal Electronic Devices), analog and/or digital discrete circuit components (transistors, resistors, capacitors, inductors, diodes, etc.), programmable logic, microprocessors, microcontrollers, application-specific integrated circuits, field programmable gate arrays or other circuit elements. A memory configured to store computer programs may be implemented along with discrete circuit components to carry out one or more of the processes described herein. We also recognize and expect advances in computing could be useful, including but not limited to, quantum devices (qbits), photonic circuits and molecular electronics. We also recognize and expect useful advances in software, including but not limited to, genetic algorithms, neural networks, GPU TensorFlow and other artificial intelligence and deep machine learning methods.

A "lock-in amplifier" is a device and/or an algorithm that demodulates the response of a system at one of more reference frequencies. Lock-in amplifiers may be electronic assemblies that comprise analog electronics, digital electronics, and combinations of the two. They may also be computational algorithms implemented on digital electronic devices like microprocessors, microcontrollers, field programmable gate arrays (FPGAs), digital signal processors, and personal computers. A lock-in amplifier can produce signals indicative of various metrics of an oscillatory system, including amplitude, phase, in phase (X) and quadrature (Y) components or any combination of the above. The lock-in amplifier in this context can also produce such measurements at both the reference frequencies, higher harmonics of the reference frequencies, and/or sideband frequencies of the reference frequencies.

"Photothermal distortion" refers to a change in the properties of a sample due to absorption of optical energy, for example the absorption of IR radiation. The photothermal distortion may refer to a change in index of refraction, reflectivity, thermal expansion, surface distortion, or other effects that can be detected with a probe beam.

"Camera" refers to an array-based photodetector comprising a plurality of photosensitive pixels. A camera may comprise one or more technology including but not limited to CCD, EM-CCD, CMOS, s-CMOS, and/or other photosensitive array technologies. The camera may support frame rates from a few frames per seconds, hundreds of frames per second, or even thousands of frames per second or higher.

"Figure of merit" refers to any metric or indicator of the relative quality of a signal or measurement. The figure of merit can for example be a measurement sensitivity, a signal strength, a noise level, a signal to noise ratio, a background level, a signal to background ratio, any combination of these, or other metric that lets one rank the relative quality of a signal and/or measurement.

Optical Photothermal Infrared (OPTIR) Imaging and Spectroscopy

FIG. 1 depicts a conventional OPTIR imaging system. Other similar systems are described in copending PCT patent application PCT/US17/63807, for example, the disclosure of which is incorporated by reference in its entirety. A region 100 of a sample 102 is illuminated with a beam of infrared radiation 104, causing a temperature rise, i.e. a photothermal response, in IR absorbing regions of a sample. To measure the photothermal response resulting from the IR absorption, at least a portion of the IR absorbing regions are also illuminated with a beam of probe radiation 106. In the configuration shown, this probe beam 106 is then reflected back along the illuminating path, and/or transmitted (108) through the sample. Both reflected and transmitted portions are indicated with arrows in FIG. 1, in addition to the illustrations of the beam waists showing the focused probe radiation 106. The change in temperature of the IR illuminated sample and/or surroundings (such as the air or fluid above or surrounding the sample) from IR absorption of the sample causes a change in the phase, polarization, intensity and/or angles of light reflected/scattered (110) from the sample, and/or the phase/polarization/intensity/angles of the light transmitted (112) through the IR absorbing regions. By measuring fluctuations in collected probe light it is possible to create a signal indicative of the absorption of IR light by the absorbing regions of the sample. In the configuration shown, probe light is collected in a reflected configuration, but measurements can similarly be performed in transmission and scattering configurations.

In many conventional systems, the probe beam can comprise a beam of visible and/or ultraviolet light, i.e. a wavelength that is significantly shorter than the IR light. The reason for the use of UV or visible light is that the shorter wavelengths of UV/visible light allows it to be focused to a much smaller spot than the IR radiation. As such it can be used to measured IR absorption with spatial resolution a factor >10× better than with conventional IR microscopy. In far-field microscopy, optical diffraction limits the spatial resolution achievable to a length scale on the order of the wavelength of light used. Specifically, the minimum detectable separation δ between two objects using the Rayleigh criterion is given by:

$$\delta = 0.61 \lambda / (n\, NA) \quad \text{Eq. 1}$$

Where λ is the wavelength of infrared light used, n is the index of refraction of the surrounding media, and NA is the effective numerical aperture of the microscope objective used. High power IR objectives usually have a maximum NA in the range from 0.7 to 0.81, setting the best achievable spatial resolution in air under the Rayleigh criterion to around 75% to 87% of the wavelength used. For example, at λ=10 μm, the spatial resolution δ is around 8 μm. The spatial resolution achievable by the OPTIR technique under Eq. 1 is set by the wavelength of the visible probe beam, not the wavelength of the IR beam. The improvement in spatial resolution achievable with the OPTIR technique is determined by the ratio of the IR wavelength to the probe wavelength. For example, with $\lambda_{IR}$=10 μm and $\lambda$probe=0.532 μm, the spatial resolution improvement for the OPTIR technique can be (10/0.532)~19λ better conventional IR microscopy with the same objective. Using $\lambda$probe=0.532 μm and the same NA as above, the OPTIR technique produce spatial resolution of around 0.4 μm. Even higher spatial resolution can be achieved with higher NA objectives, for example an objective optimized for visible light microscopy and/or using shorter wavelength probe beams, for example in the blue/UV range.

In some embodiments, brief periodic pulses of IR illumination (on the order of hundreds of nanoseconds) used. The use of brief IR pulses in combination with synchronous detection techniques can provide high sensitivity and spatial resolution. The signal indicative of IR absorption can be measured as a function of the wavelength of IR radiation to generate IR absorption spectra and the IR absorption signal can be measured as a function of relative sample position to generate spatially resolved maps of chemical composition of the sample. Spatially resolved maps can be created by measuring IR absorption at select wavelengths (or equivalently wavenumbers) as a function of sample position, and/or entire IR absorption spectra can be measured at multiple locations on a sample. In this case of so-called hyperspectral imaging, the data cube has transverse dimensions x and y along the sample surface while the third dimension comprises IR absorption spectra which is used to identify molecules by their excitation modes (stretching, bending, twisting, etc.).

A key limitation in the prior art of photothermal imaging and spectroscopy, however, has been measurement throughput. Photothermal spectra are typically taken at the rate of 0.1 to 100 seconds per spectrum. While this can be acceptable for point spectra or small arrays of spectra, this measurement time becomes unacceptable for large numbers of spectra, for example a hyperspectral array comprising thousands or even millions of spectra. Described below are embodiments to achieve high throughput OPTIR measurements by enabling parallel measurements at a plurality of points on a sample simultaneously.

Figure 2:
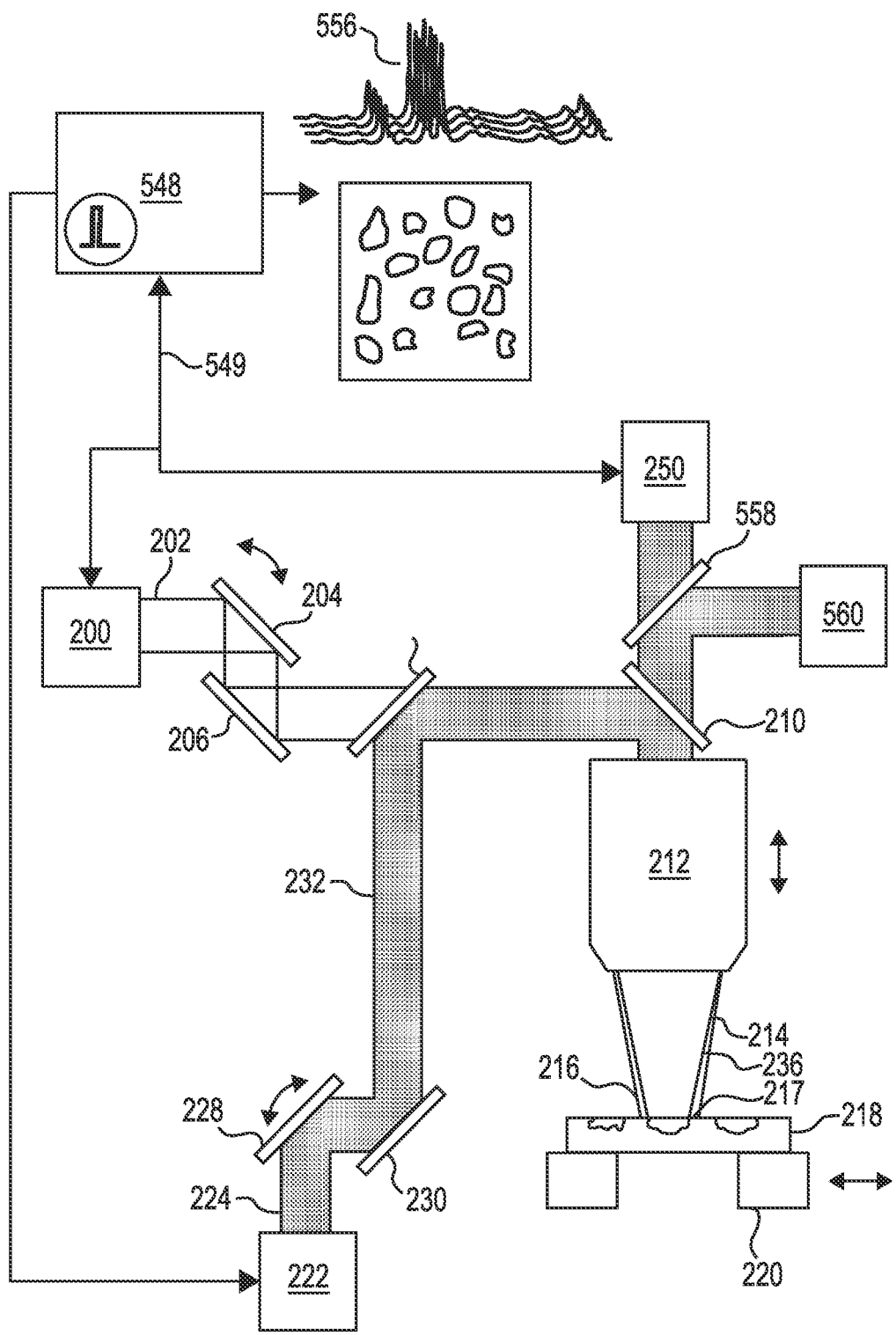
FIG. 2 is a simplified schematic diagram of a of an embodiment of a widefield OPTIR system.

FIG. 2 shows an embodiment of an OPTIR device arranged for widefield measurements. In this embodiment an infrared (IR) light source 200 produces a beam of IR light 202 that is optionally directed by one or more mirrors 204 and 206 before passing through beam combiner 208 (typically a dichroic beam splitter although a polarizing beam splitter could also be employed). In the configuration shown, the beam combiner 208 is substantially transmissive to IR radiation and reflective to probe radiation, thus the IR beam passes to dichroic 210. The beam combiner can alternately be reflective to IR and transmissive to probe light, and the configuration can be adjusted accordingly. Dichroic 210 reflects IR light to focusing element 212, to focus a beam of IR radiation 214 to a spot 216 on a region of a sample 218. The sample 218 may be mounted on a translation stage and/or scanner 220 to change the position of the sample 218 relative to the IR beam 214. A probe beam source 222 generates a beam 224 of ultraviolet and/or visible light. The probe beam 224 is directed to optional mirrors 228 and 230. After the optional mirrors, the probe beam 232 goes to beam combiner 208.

In the configuration shown, the probe beam 232 is reflected to the right by beam combiner 208, to dichroic 210, and then to focusing optic 212. Focusing optic 212 focuses a probe beam 236 into a focused spot 217 of the sample 218, generally at least partially overlapping with the focused spot 216 of IR beam 214. In alternate configurations, the IR and probe beams can be delivered to the sample by separate focusing optics. As will be discussed below, in this embodiment, at least the probe beam and optionally also the IR beam are arranged to illuminate a wide area of the sample. That is, unlike conventional OPTIR measurements, the probe beam is not focused to a single diffraction limited spot, but instead is configured to illuminate a wide area or at least a plurality of locations simultaneously to enable parallel measurements of IR absorption at a plurality of locations on the sample simultaneously. In one embodiment the IR and probe beams both illuminate an area of the sample exceeding 100 microns in diameter.

At least one of mirrors 204, 206, 228 and 230 is preferably electronically controllable to adjust and optimize the overlap of focused IR and probe light beams 202 and 224 to generate overlapping IR beam 214 and probe beam 234 at the sample 218. The overlap need not be symmetric or one centered on the other.

Probe light reflected or scattered from the sample can be collected by a collecting optic or "collector." The collector may comprise focusing optic 212, i.e. the same optic can be used to illuminate the sample and collect light from the sample. To achieve high spatial resolution, it is desirable that the collector have a high numerical aperture. For example, the collector may comprise an objective with a numerical aperture of at least 0.4, or more preferably greater than 0.6. In one embodiment, the collector is a Cassegrain style reflective objective with 40× magnification and with an NA of 0.78. In another embodiment, the collector is a Cassegrain objective with 20× magnification and an NA of 0.70. The arrangement in FIG. 2 has a significant advantage in that it allows the collection of specularly reflected light, as well as all scattered light within the numerical aperture cone of the collector. This means that the embodiment shown in FIG. 2 has the ability to capture the most intense portions of probe light returning from the sample and hence can generate a strong signal indicative of IR absorption by the sample, and at sub-micron spatial resolution. Using the numerical apertures indicated above, the resolution given by Eq. 1 are 0.42 µm with the 0.78 NA objective and 0.46 µm for the 0.70 NA objective. The high NA objectives generally have short working distance, often as short as a few mm or less. The short working distance makes the back-reflecting configuration shown in FIG. 2 advantageous since the close proximity of the objective to the sample dramatically limits access for other off axis collection paths.

In other embodiments, IR refractive objectives may also be used instead of reflecting objectives. For example, Pike Technologies manufactures refractive objectives 20×0.60 NA and 40×0.85 NA. Compensation optics can be employed in either the probe or IR beam paths to compensate for the difference in focal length/dispersion between IR and probe wavelengths. Alternately probe light that is reflected, transmitted, scattered or otherwise interacted with the sample can be collected by other collection optics, not shown. For samples that are transparent to the probe light, another collection objective may be placed below the sample to collect probe light transmission. This is advantageous for highly transparent samples as it allows collection again of a large portion of probe light after interacting with IR absorbing regions of the sample. In this case the collection objective can be a high NA visible objective. This can also be beneficial for spatial resolution, as visible objectives are available with numerical apertures in excess of 0.9 NA. A 0.9 NA objective collector used in a transmission configuration can give a spatial resolution of 0.36 µm at 532 nm probe wavelength.

Back to the reflection configuration shown in FIG. 2, collected probe light is then reflected back towards filter mirror 210. Filter mirror 210 can be partially reflecting, e.g. a beamsplitter to allow a portion of the reflected light to be directed towards camera 250, or similar array detector. Camera 250 is used to measure the change in collected probe light resulting from IR absorption by the sample at a plurality of locations on the sample in parallel.

Controller 252 is used to perform several functions. First, controller 252 synchronizes the IR source 200, probe beam source 222 and camera 250 with trigger signal 254. Specifically, the trigger signal ensures that (1) camera frames are exposed in sync with IR laser pulses; and (2) that the probe beam is not unnecessarily exposing the sensor in camera 250 in a way that would lead to camera saturation. The triggering scheme is discussed in more detail below.

Controller 252 or a separate controller (not shown) is used to collect data from the camera 250 to determine the photothermal response of the sample due to IR absorption, thus enabling measurements of signals indicative of IR absorption by the sample. By measuring this IR absorption signal as a function of wavelength, or equivalently wavenumber, IR absorption spectra 256 can be measured, providing chemical characterization and material identification of chemical components of the sample. IR absorption of the sample can be made at a plurality of locations on the sample, using the parallel measurement capability of the camera 250 and/or by repeating measurements at multiple locations of the sample scanner 220.

There are several challenges associated with performing widefield measurements of IR, specifically related to using a camera/array detector in place of a single point detector. To enable IR absorption measurements on multiple locations on the sample simultaneously with sub-micron spatial resolution using the OPTIR technique involves issues with including dynamic range, sample illumination, and spatial resolution, and other factors. Each of these in turn will be discussed below.

Sensitivity and Dynamic Range

Achieving sufficient sensitivity using camera-based detectors versus single point detectors can be a challenge since the photothermal response can be very small, i.e. smaller than can be detected within the dynamic range of a typical camera. For example, changes in index of refraction and thermal expansion are roughly $10^{-4}$/K for polymeric materials, and smaller for many other materials. The change in detected probe beam intensity is generally of similar order of magnitude to these fractional changes in index/expansion coefficient, that is the collected probe beam intensity also changes by roughly by $10^{-4}$/K. It is often desirable to minimize the sample temperature increase to limit the chance for thermally induced changes in the sample. So a good target is to have a temperature increase of less than 10K, thus making the maximum fractional change in index of refraction or thermal expansion around $10K \times 10^{-4}/K = 10^{-3}$. In IR spectroscopy it is also desirable to have a large dynamic range to accommodate the difference in absorption between the strongest absorption bands and the weaker bands. For example, a weak IR band may be 10-100× smaller than a strong band. To resolve 100× weaker band with a SNR of 10 would then require the ability to detect fractional changes of $10^{-3}/10/100 = 10^{-6}$. Unfortunately, this implies a dynamic range of $10^6$, well beyond most if not all commercially available cameras. Cameras have a finite well depth that sets the maximum number of photoelectrons that can be accumulated before the exposure must be stopped and the camera pixels read out. The dynamic range of a camera sensor is set by the ratio of the well depth and the pixel read noise. High end scientific CMOS cameras have a dynamic range in the range around 10,000 to 60,000, several orders of magnitude below that required to perform high speed IR spectroscopy with a dynamic range sufficient to resolve minor bands.

Sufficiently high dynamic range can be achieved by accumulating multiple frames. In this case the signal increases linearly with the number of frames accumulated, while the noise partially cancels out, growing only like the number of square root of the number of frames. Thus the dynamic range grows like the square root of the number of frames accumulated. So for example to achieve a dynamic range of $10^6$ with a camera sensor with a dynamic range of 50,000 would require an accumulation $(10^6/50,000)^2 = 400$ frames. Multiple camera frames can be accumulated by controller 252 and/or with additional optional frame summing electronics not shown, for example comprising an FPGA, embedded computer, or other electronics that can capture and sum frames.

Throughput

We turn next to measurement throughput achievable under embodiments described herein. For widefield photothermal measurements, the relevant figure of merit for the camera is the total time t required to achieve a desired dynamic range DR, given the cameras intrinsic dynamic range $DR_0$. This measurement time t is given by:

$$t = (DR/DR_0)^2/f$$

where f is the frame rate of the camera. Different cameras also have dramatically different frame rates, ranging from a few 10 s of frames per second up to many thousands of frames per second or higher. Higher frame rates are not necessarily better if they come at the cost of significantly worse dynamic range. Scientific CMOS cameras can have a good balance of frame rate and dynamic range. For example, using a camera like the Tucsen Dyhana 95 has a dynamic range of around 62,100, and a frame rate of 192 frames/second for 256×256 pixels. Using the equation above, a dynamic range of $10^6$ can be achieved in 1.35 seconds. To acquire a spectrum comprising photothermal measurements of IR absorption at 500 different IR wavelengths would then take 500×1.35 sec=676 seconds. While this is much longer than the time for a single point OPTIR spectrum with a single point detector (typically in the range of 1-10 seconds), the fact that these measurements are performed in parallel provide a significant net benefit over single point measurements. In the scenario above, the camera sensor can acquire 256×256=65,356 spectra simultaneously. So the throughput under this embodiment is 63,356/676=97 spectra per second with a dynamic range of $10^6$. This represents a spectral rate of 100 to 1000× faster than obtaining OPTIR spectra with a single point detector at the rate of 1-10 seconds per spectrum mentioned above. As such a wide field approach can achieve dramatically higher measurement speeds despite the lower intrinsic dynamic range. Embodiments described here can measure IR absorption at a plurality of locations on a sample simultaneously with a spectral throughput of greater than 20 spectra per second, greater than 50 spectra per second, and greater than 90 spectra per second, while achieving dynamic ranges for the spectra as high as $10^4$, $10^5$, and $10^6$.

In some embodiments it can be desirable to accumulate camera frames both when the IR light source is pulsed on and accumulate frames when the IR light source is off. Accumulating frames with IR light on and IR light off can be used to create a differential measurement indicative of the change in collected probe light due to sample IR absorption. In some configurations, the camera system may have on-board memory to accumulate multiple frames, thus reducing the required frequency of data transfer to the host. It may be possible to also accumulate two or more separate images on the camera, e.g. one accumulator for frames with the IR on and another accumulator for frames with the IR off. Some cameras also have the ability to acquire two different image buffers with a variable delay between the camera exposures for the two buffers, for example the Princeton PI-MAX® brand cameras. In this configuration an initial trigger signal can trigger the first acquisition, e.g. the probe beam response to the IR pulse and a second image buffer is accumulated a short delay afterwards, e.g. after the thermal relaxation has occurred and the probe intensity is back to a baseline value. The two images may be subtracted or otherwise compared to determine the spatially resolved photothermal response due to IR absorption by the sample.

Alternately, camera data can be turned into a time based data stream that be synchronously demodulated, for example using digital lock-in techniques and/or computations intended to simulate a lock-in, i.e. multiplying time dependent data by one or more periodic basis functions (e.g. sines and cosines, gate pulses, wavelets or other functions) and then filtering the resulting output. In any of these cases, the goal is to determine dynamic changes in the camera measurements of collected probe intensity to determine a signal indicative of the IR absorption of regions of the sample, via the IR absorptions modulation of the collected probe light.

Sample Illumination

In one embodiment, the IR and probe beams are configured to illuminate an area of with a diameter of roughly 100 µm. In other embodiments, areas as large as 1 mm across can be illuminated by IR and probe beams. Choosing an illumination area of around 100 µm has several advantages. First, that illumination area is only a few times larger than the diffraction limited spot size of an infrared beam used in conventional OPTIR instruments. For example, a focused IR spot size may be in the range of 10-30 µm, depending on the NA and quality of the focusing objective used. So expanding the IR beam to around 100 µm in diameter only increases the beam area by 10-100×. To maintain the same IR optical power density as used in convention OPTIR measurements thus requires 10-100× more IR power than currently used for single point measurements. Typical OPTIR single point measurements are made with around 5-20 mW of peak power (i.e. power during the IR pulses).

Available tunable sources in the mid-IR can produce output beams on the scale of several hundred milliwatts to many watts of optical power. For example, the Firefly-IR from MSquared Lasers can produce >250 mW average power of mid-IR radiation. Nanosecond optical parametric oscillators (OPO) for example from Ekspla can produce 450 uJ at 1 kHz or 450 mW of IR power. Amplitude Systemes produce an OPO laser that can take up to 50 W of input power and produce mid-IR output with >12% efficiency, producing for example 6 W of mid-IR energy. Jiang et all have demonstrated high power pulsed OPOs with up to 8.5 W of power at 3.3 um wavelength (DOI:10.1364/OE.23.002633). Peng et al. demonstrated a tunable mid-IR laser with output power in excess of 27 W (DOI:10.1134/S1054660X1201015X). Hemming et al. demonstrated a high power mid-IR ZGP ring OPO with over 30 W of optical power (DOI: 10.1364/CLEO_SI.2013.CW1B.7).

Each of these mid IR sources would in turn provide sufficient power to illuminate increasingly larger areas of the sample with the same average power density as used for the microscopic focus case. For example, assume that for the microscope case we focus the IR beam to a 10 µm spot with 1 mW of power for sufficient sensitivity. With 30 W of IR power from the Jiang et al. OPO, we could illuminate an area with a diameter 122× bigger than with a 10 µm focused spot (via the square root of the power ratio of 30 W to 1 mw). So this would correspond to the ability to illuminate a circular area 1220 µm in diameter. The net effect is that there are multiple IR sources that are strong enough to illuminate a wide area on the scale of 100 µm across, and some sources sufficient to support a circular area larger than 1 mm in diameter. Larger beam IR beam sizes can be generated by using a beam reducer to reduce the effective numerical aperture of the IR beam focusing, and/or by illuminating an IR compatible diffuser. Low cost thermal sources, for example a globar naturally illuminate larger areas of the sample due to their extended size. These sources can be made suitable for OPTIR measurements at high spatial resolution by coupling them to high speed modulators, for example photoelastic modulators and high-speed choppers. For example Hind Instruments make suitable photoelastic modulators and Scientec makes optical choppers that can modulate a beam in excess of 100 kHz.

On the visible side, changing from roughly a 1 µm area to a 100 µm area, involves ~100,000× larger illumination area. One might think that this results in the need to illuminate with 100,000× more laser power. Conventional single point OPTIR measurements are performed with input probe powers ranging from around 1-100 mW, so requiring 100,000× more power could be prohibitive. There are several aspects that can make mitigate this and can reduce the required probe power, however. A Tucsen Dyhana 95 has 95% quantum efficiency and a full well capacity of 90,000 photoelectrons. At 532 nm wavelength, this leads to a saturation dose of 2 nJ for 256×256 pixels. Operating at the maximum frame rate for the Tucsen Dyhana 95 camera of 192 frames per second, this means that the saturation does can be delivered every ¹⁄₁₉₂ sec=5 msec. A 2 nJ exposure every 5 msec is equivalent to an average probe power over the camera of 2 nJ/5 msec=0.4 µW. By comparison, probe power levels incident on a single point detector in a conventional OPTIR measurement are of order 20 to 400 µW (depending on the sample reflectivity and damage thresholds). So the camera pixels will saturate at power levels up to 50-1000× lower than typically used in a single point detector. This means that using a camera based detector can dramatically lower the average power per pixel requirement.

Assuming a 2 nJ saturation dose or 0.4 µW average power target, we can estimate the input pulse energy/power required. Assuming a 4% sample reflectivity, a 60% optical throughput through the Cassegrain objective in both directions, two beamsplitter losses at 50% each, and an 80% optical throughput elsewhere, we arrive at an estimate of requiring roughly 400× more input power than is detected at the detector. Thus we need a probe beam source that can supply around 800 nJ per pulse or 160 µW average power. This is in fact a fairly modest amount of power, and not 100,000× more input than used with a single point detector as would appear necessary on first impression. There are several visible probe sources that may be suitable. For example gas lasers, diode lasers, superluminescent diodes, LED light sources and others can supply sufficient optical power for this application. Other incandescent sources could also be used. Higher power sources do, however, provide an additional advantage, related to supporting shorter probe pulses that can improve spatial resolution.

Spatial Resolution and Thermal Diffusion

Shorter probe beam pulses are advantageous for maintaining high spatial resolution. Thermal diffusion can in principal compromise spatial resolution is the heat generated in IR absorbing regions diffuses to neighboring non-absorbing regions of the sample. By using short probe beam pulses, it allows measurements of the photothermal response at selected time windows after the start of the IR pulse. The thermal diffusion length L is given by:

$$L = (\alpha t)^{1/2}$$

where L α is the thermal diffusivity of the sample material and t is the diffusion time. For example, assuming a thermal diffusivity of $10^{-7}$ m$^2$/sec (typical of polymers), the thermal diffusion length corresponding to the duration of a 200 µsec long probe pulse would be around 4 µm, whereas a 2 µsec probe pulse would lead to a thermal diffusion time of around 0.4 µm.

Figure 3:
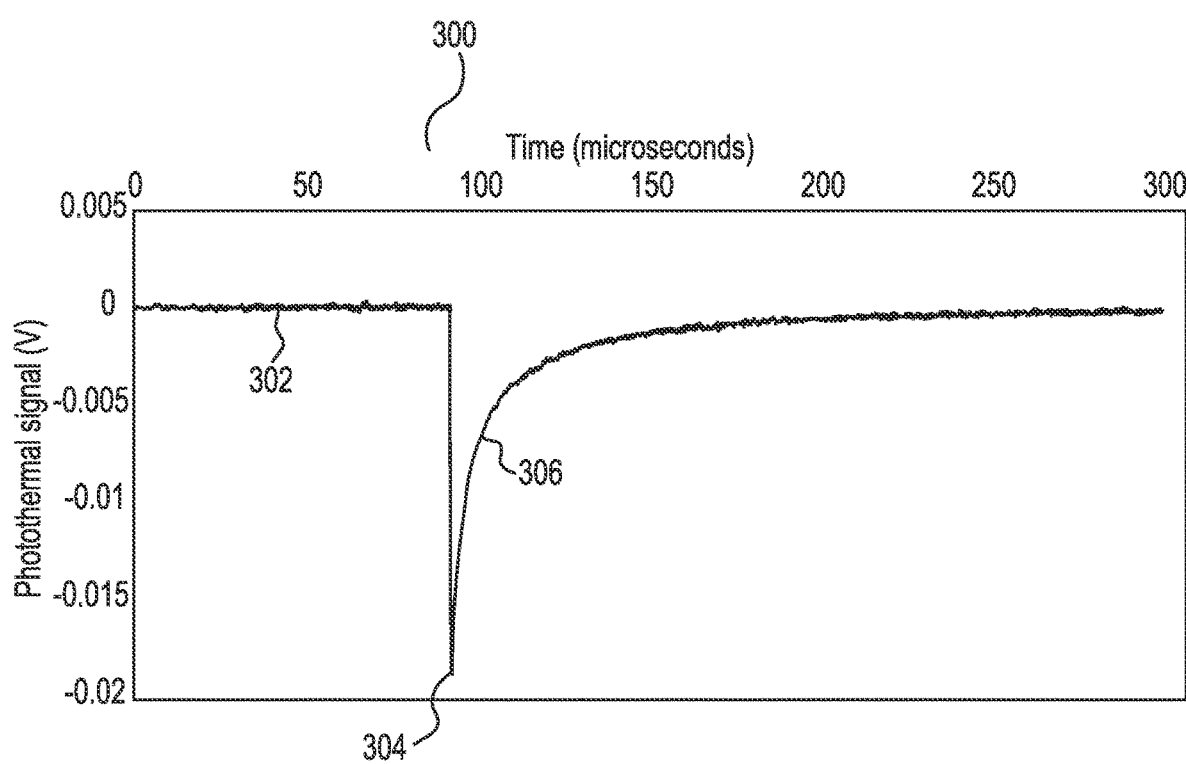
FIG. 3 is an example of a time resolved measurement of a photothermal response to IR absorption.

FIG. 3 shows a photothermal response 300 on a polymer film captured with a single point detector in a time resolved measurement. For the measurement in FIG. 3, a polymer film was irradiated with an IR pulse at 1729 cm-1 from a quantum cascade laser (QCL) based IR source with a pulse duration of 260 nsec while the intensity of the reflected probe light was measured with a single point silicon detector. In the configuration used, the probe beam intensity dropped sharply during the IR pulse duration (point 304) relative to the intensity before the IR pulse (302). The resulting thermal relaxation is observed in 306 as the probe signal returns to the baseline. FIG. 3 has been plotted to only show the AC change in the collected probe light (i.e., the baseline is shifted to zero).

FIG. 3 shows that the photothermal response of the sample can last for in excess of 100 µsec. To maximize the total detected signal, it may be desirable to integrate the photothermal response over the entire decay time (or a substantial fraction thereof). If the photothermal response is integrated over extended times, however, the spatial resolution can be compromised by the spreading of heat into neighboring non-IR absorbing regions. In some embodiments, it is desirable to construct an IR absorption signal using the photothermal response corresponding to short times after the IR laser pulse, so as to limit loss of spatial resolution to thermal diffusion. This can be achieved in several ways. First, it can be achieved by rapidly recording the collected probe over a plurality of times and then constructing an IR absorption signal with probe beam measurements selected only from a gated duration over selected period of time after the start of the IR pulse. Alternately, it is possible to achieve a similar result use a short camera exposure, selected to start synchronously with the IR laser pulse. In this case the camera exposure time and phase acts as the gate. In one embodiment, the probe beam is also synchronously pulsed and the effective camera exposure time can be controlled by the duration of the probe beam pulse. In any of these cases, it is possible to adjust the gate time (e.g. probe beam pulse duration and/or camera exposure time), to optimize between spatial resolution and sensitivity.

Figure 4:
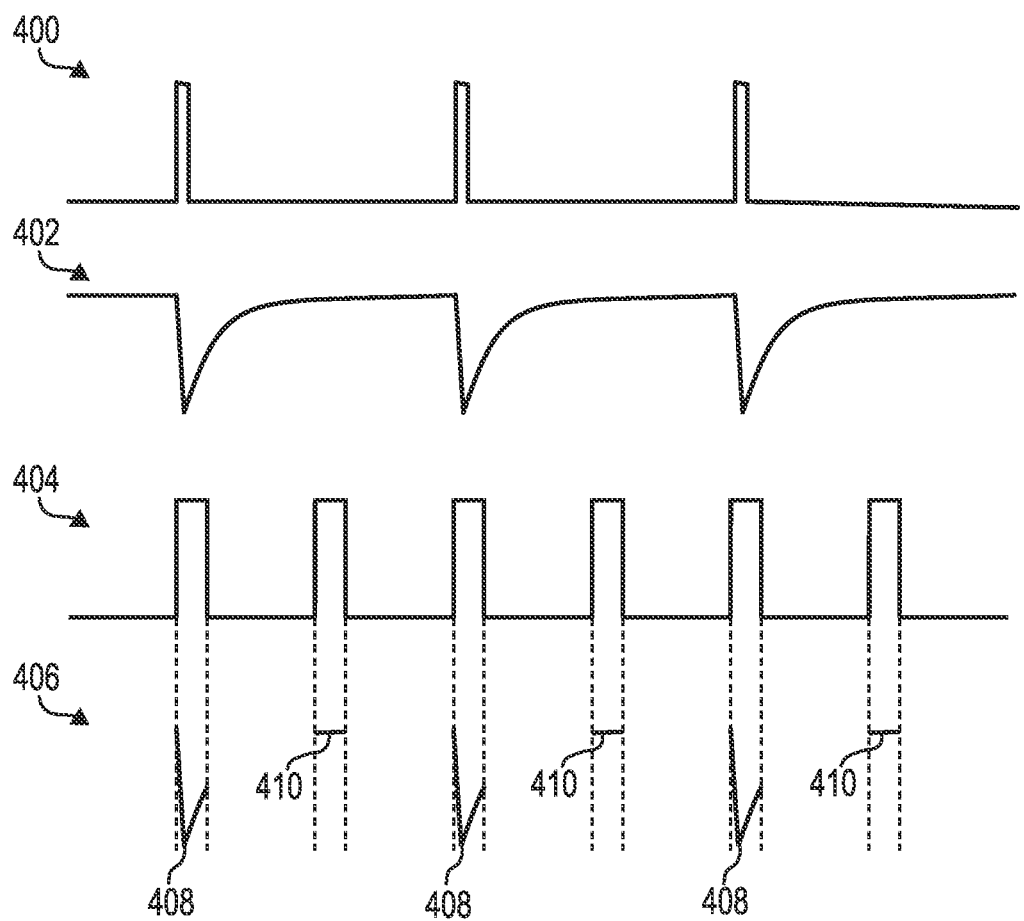
FIG. 4 shows an example of gating of an IR absorption signal from a probe beam.

FIG. 4 shows an example of gating that can be used in the construction of an IR absorption signal from the probe beam. Trace 400 shows an example pulse train for a trigger pulse for an IR source, e.g. the synch or trigger input to a pulsed laser source. Trace 402 shows an illustration of the intensity of collected probe light as a function of time. As in FIG. 3, trace 402 shows a sharp decrease in collected probe light during the duration of the IR pulse, and then a more gradual thermal decay back to the baseline. Trace 404 shows an example gate function that can be used to select portions 406 of trace 402 to use for the calculation of a signal indicative of IR absorption by the sample. Note that in the example shown, the gate pulses in trace 404 are optionally arranged to happen twice as often as the IR pulses and photothermal response in 400 and 402. The reason for this is to enable a differential measurement. Specifically, the probe beam intensity can be sampled alternately in two different situations: (a) in response to IR absorption, e.g. the portions 408 of trace 406; and (b) during a baseline period before or after an IR pulse, for example portions 410 of trace 406. The two signals IR on (408) and IR off (410) can be subtracted or otherwise compared to create a differential signal indicative of the change in the photothermal signal in response to IR absorption, and thus indicative of the amount of IR absorption. The gate pulses shown in trace 404 can be used in several ways. For example, it can be used in a time resolved measurement to select the regions of interest in trace 402 to select the portions 408 and 410 in trace 406. Alternately, gate pulses 404 can be used to set the camera exposure start and end times. The gate pulses can also or instead control the emission time for probe beam pulses. For example the gate pulses can be used to modulate the diode current in an LED based probe light source or in a diode pumped solid state laser or other probe light source with electronically controllable output. The gate pulses alternately control a shutter and/or modulator placed in front of the camera and/or the probe beam light source. Electro-optic modulators, acousto-optic modulators, photo-elastic modulator, high-speed choppers and other related devices are examples of devices that that can be used to periodically modulate the intensity of a CW laser source to provide probe light pulses to illuminate the sample synchronously with the IR light pulses.

The length of the gate time can determine what fraction of the thermal decay is sampled. To optimize for spatial resolution, it may be desirable to use short gate times. For example, to correspond to a thermal diffusion length of less than 0.5 µm, it can be desirable to employ a probe beam pulse of less than 2 µsec, as described above. The peak probe beam power required it is set by the desired probe pulse energy divided by the pulse duration. So if we want 2 nJ probe energy delivered in 2 µsec (such that we fill the camera pixel wells within a 2 µsec thermal diffusion time), we need peak power to the camera of 2 nJ/2 usec=1 mW. Applying the 400× factor previously discussed regarding the optical losses between the probe source and the camera, this suggests the probe beam source should provide at least 400 mW of optical power for 2 µsec to be able to achieve optimal spatial resolution and make best use of the dynamic range of the camera sensor.

High brightness LED sources are also available that can be suitable. LED light source for the probe beam can be advantageous as the incoherent light source can minimize speckle and interference artifacts. Thorlabs, for example, makes single color high power LED illuminators for microscopy e.g. their SOLIS brand products that produce up to 3-7 W of light with many wavelength options, and the ability to be pulsed and/or modulated at frequencies at frequencies up to 250 kHz with available LED power supply/controllers. Based on laboratory measurements, 7 W of optical power from an LED microscope illuminator through a 40×0.78 NA Cassegrain objective onto an optically transparent polymer film returns enough light to a camera to saturate the central region a scientific CMOS camera sensor within 70 microseconds. Thus, a 7 W LED source is sufficient to provide enough light pulses as short as 70 µsec while still using the maximum dynamic range of the camera sensor. (These measurements were performed on a testbed system with many optical surfaces and associated losses. As much as 2× better optical throughput can be achieved with an optimized design with a minimum number of optical surfaces and appropriate low loss coatings.) For highly reflective samples or samples measured in transmission, the amount of collected probe light can be much higher. For example, while a transparent polymer may only reflect around 4% of the incident probe light, a highly reflecting sample or a sample on a highly reflective substrate might reflect 90+% of the incident probe light, leading to ~22× more light detected by the camera. This would enable probe light pulses as short as 70 μsec/22=3.2 μsec. Similar results can be obtained in transmission for samples that are largely transparent at the probe light wavelength. Note that it is not absolutely necessary to maximize the dynamic range of the camera pixels. If achieving highest spatial resolution is the primary goal, short probe beam pulses can be used, such that the collected light is even well below the camera pixel well depth and then more camera frames can be co-added to achieve the desired dynamic range.

High power laser sources are also available with sufficient intensity to illuminate a wideregion of a sample. Visible, UV and near IR pump lasers are available with extremely high power as well. For example, 532 nm green laser systems are available from Optotronics with up to 6 W of power. Other low-noise scientific lasers with powers >20 W are available. Coherent manufactures a 1064 nm laser with up to 55 W of optical power.

Figure 5A:
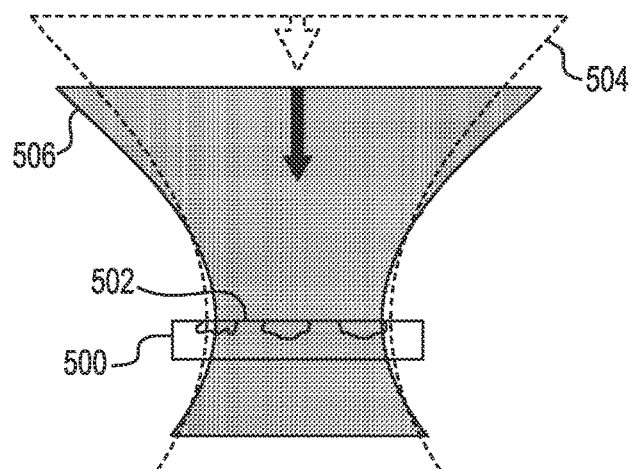
FIGS. 5A-5C show probe beam illumination according to three embodiments.
Figure 5B:
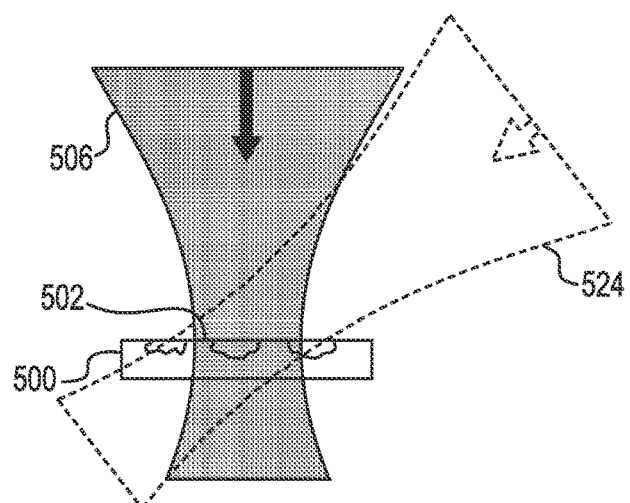
Figure 5C:
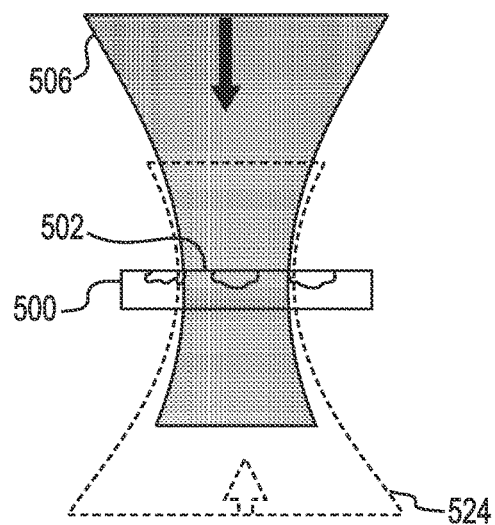

The probe beam illumination can be configured in several different ways. FIGS. 5A, 5B, and 5C show three configurations. FIG. 5A illustrates a subset of an embodiment of the current invention in which a sample 500 has a region 502 which is top illuminated with significantly overlapping IR beam 504 and probe beam 506 over an area that exceeds the spatial resolution of the imaging system and allows for simultaneous detection of IR absorption from a plurality of points within the illuminated area. This illustration shows illumination as Gaussians with the waist at the surface. However, a more uniform illumination is preferred (also known as a Top Hat intensity profile) and this may be generated in a number of ways, including the combination of a Gaussian and donut laser modes.

FIG. 5B illustrates an alternate embodiment where the IR beam 524 is brought in from the side. Side illumination of IR becomes very practical, given the low NA required to deliver a spot that is about 1 mm diameter. Elongation in one axis may yield an ellipse on the surface that is 2 or 3 times longer than it is wide. Side IR beam delivery allows for better objectives that only operate in the visible (refractive not reflective). For example, the focusing element 212 of FIG. 2 can be a visible/refractive objective. High NA objectives for 532 nm light are plentiful and reasonably priced. The 100× Mitutoyo Plan Apochromat has a 0.7 NA and 6 mm working distance, enabling sufficient access for side IR beam delivery. Refractive objectives can also provide better imaging and optical throughput than an IR compatible Cassegrain style objective.

FIG. 5C illustrates an alternative embodiment in which the two beams are counter-propagating. In this case, IR beam 534 is shown illuminating the sample from below, e.g. through an IR transparent substrate, whereas the probe beam 506 illuminates the sample from above. In this case, it may be advantageous for the camera to be positioned to collect probe light that is transmitted through the sample. It is also possible to switch the IR and probe beam configurations in both FIGS. 5B and 5C, for example having the probe beam illuminate the sample from an angle in FIG. 5B and the IR beam be orthogonal to the sample. And in FIG. 5C, it is possible to have the IR beam coming from above and the probe beam from below.

Figure 6:
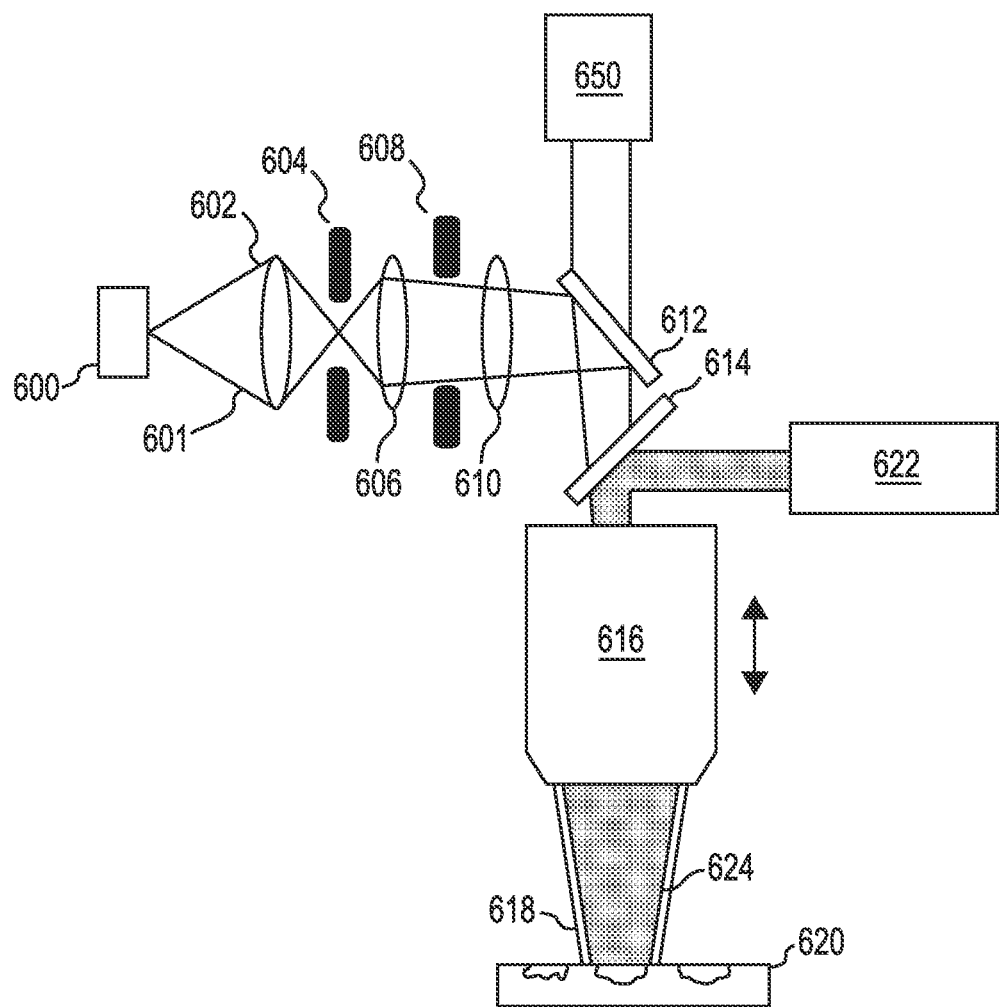
FIGS. 6-8 show various illumination schemes according to embodiments.

The widefield illumination by the probe beam can be achieved in many possible configurations. In one embodiment, a conventional Kohler illumination scheme can be used to project an image of the probe illumination source on the back focal plane of the focusing objective, for example focusing element 212 in FIG. 2. A simplified schematic diagram of such an arrangement is shown in FIG. 6. In FIG. 6, a probe beam source 600, for example a visible light LED emitter, generates a beam of probe light 601, at least a portion of which is collected by a first collection lens 602, for example an aspheric lens. The collection lens and optionally in combination with other optics, focus an image of the probe light source 600 in an image plane in the vicinity of aperture diaphragm 604. This image of the probe light source is then related by one or more lenses, for example lenses 606 and 610 to create an image of the probe light source in the vicinity of the back focal plane of objective 616. The arrangement of the collection lens and other lenses can be arranged to produce an image of the probe light source at the back focal plane of the objective 616 that is appropriately matched to the input pupil of the objective. Optional field diaphragm 608 can adjust the area of the sample illuminated by the probe beam. For more uniform illumination by the probe beam, it may be desirable to make the image of the probe beam somewhat larger than the input pupil, for example 20-50% larger, depending on the desire for uniform illumination versus the requirement for optical throughput. An IR source 622 can be collinearly combined with the probe beam using dichroic mirror 614. Optional beam steering mirrors, for example 204, 206, 228 and 230 in FIG. 2 are not shown in FIG. 6, but may be used to control and optimize the overlap between the IR and probe beams. Thus an IR beam 624 and a probe beam 618 can be focused on the sample to illuminate a large area of sample 620. Probe light scattered and/or reflected from the sample may be collected by camera 650 and analyzed as described above to create a signal indicative of IR absorption of a plurality of locations on a sample.

Figure 7:
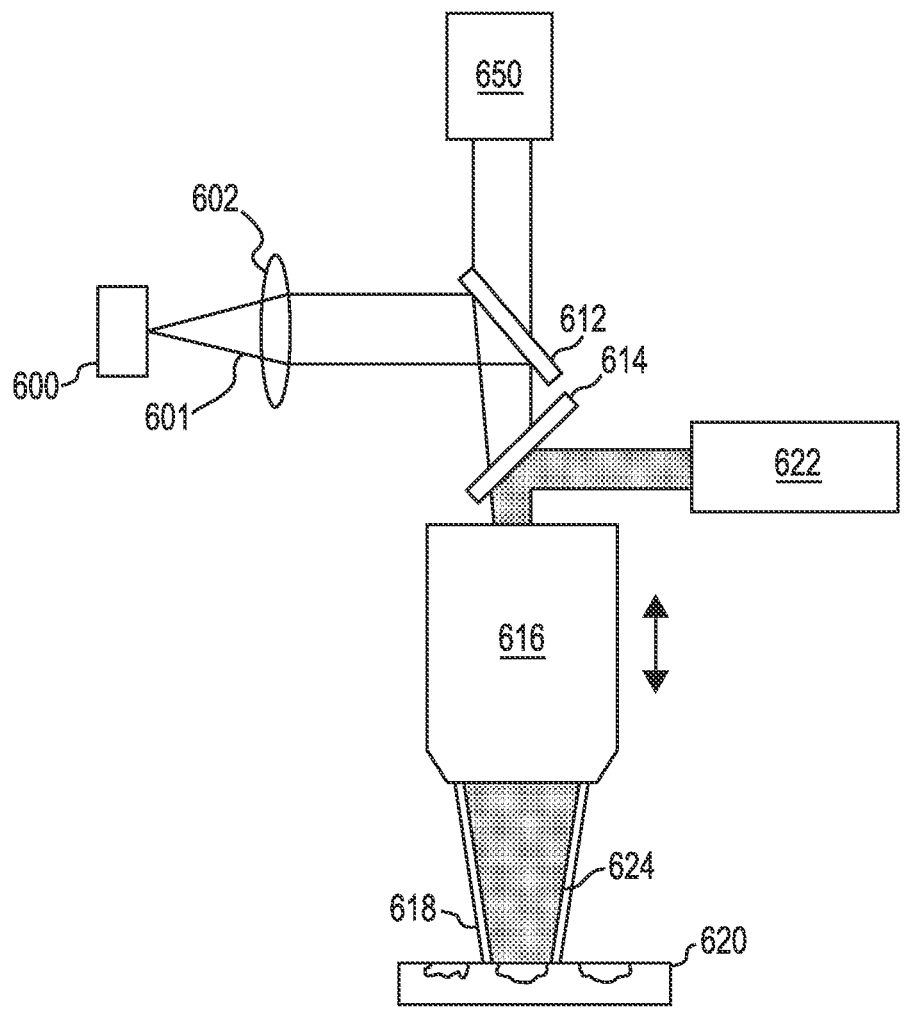

Alternately, critical illumination schemes can be employed, for example directly forming an image of the probe beam source (e.g. an LED emitter) onto the sample. FIG. 7 shows a simplified schematic diagram of this arrangement. FIG. 7 is substantially similar to FIG. 6, employing the same numerical callouts, and associated descriptions apply as appropriate. In FIG. 7, however, a simplified illumination scheme is used. In this scheme probe beam source 600 is imaged onto the sample 6520 directly using the combination of collection lens 602 and objective 616. The image of the probe beam source can be magnified or demagnified as desired based on the relative size of the probe beam source emitter versus the desired size of the illuminator. For example, for a 1 mm LED emitter, a 10× ratio of focal lengths between the collection lens and the objective focal length would lead to a projection of a 100 μm diameter image of the LED emitter on the sample surface. In another embodiment, an LED emitter can be placed directly above the sample, for example mounted on the bottom of focusing element 212.

Figure 8:
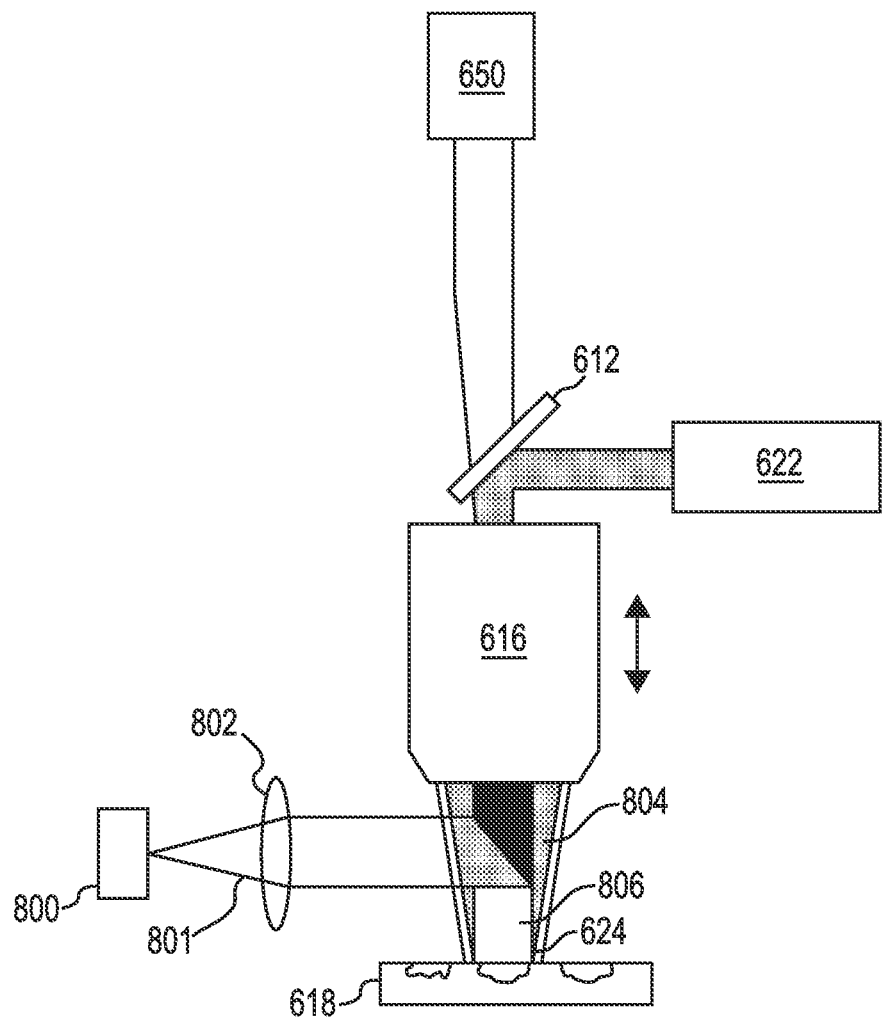

FIG. 8 shows an alternative embodiment for providing IR and visible illumination to the sample. FIG. 8 is similar to FIG. 6, employing some of the same numerical callouts, and associated descriptions apply as appropriate. In FIG. 8, probe beam source 800 produces a beam of probe light 801 that is incident on one or more optional lenses 802 that can be used to collect, collimate, magnify/demagnify, and/or focus light from the probe beam source 800. The probe beam 801 is then incident on a small mirror 804 that directs the probe light beam 806 to sample 618. In the case of a Cassegrain objective used for focusing element 616, there is a central obstruction in the objective. So a mirror 804 can be attached or otherwise placed on the bottom of the objective 616 without obstructing the path of the IR light beam 624 also being directed toward the sample.

Figure 9:
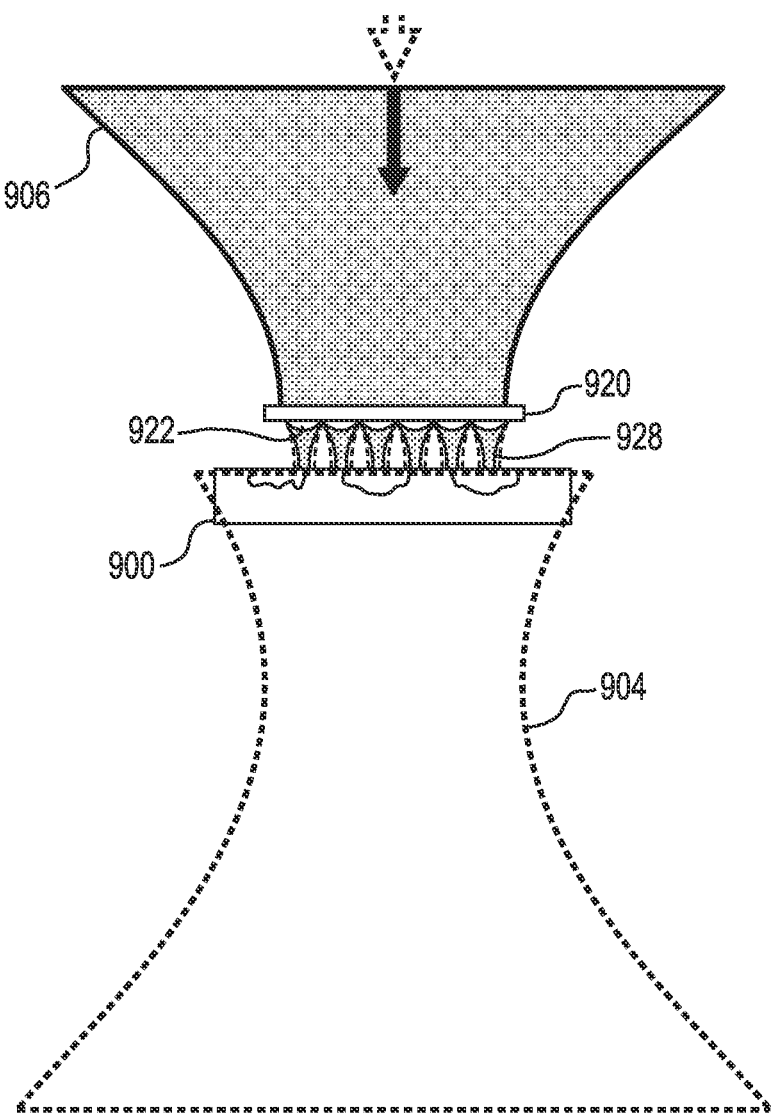
FIG. 9 shows an embodiment in which multiple discrete sampling locations over a wide area are simultaneously measured.

FIG. 9 shows an example of an alternative illumination scheme using a lenslet array to provide an array of discrete illumination points. In this embodiment, sample 900 is illuminated from below by IR beam 904. Probe beam 906 is directed toward the sample 900 from above. Before the probe beam 906 strikes the sample, however, it strikes a lenslet array 920 with a plurality of small lenses 922. Each lens 922 creates a discrete focus 928 that illuminates a portion of sample 900. A wide area of the sample can be measured by repeating measurements at a plurality of locations of the sample, e.g. by raster scanning the sample on a sample scanner, as shown in FIG. 2. The scanner need only have a range corresponding roughly to the separation between lenslet focus spot to be able to generate a contiguous image of IR absorption properties of the sample.

Figure 10:
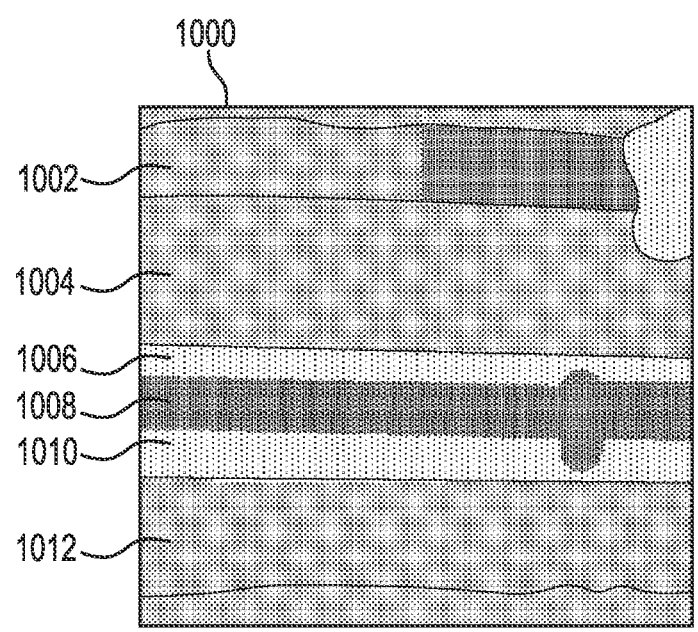
FIG. 10 shows an output depicting various substances detected by a sensor according to an embodiment described herein.

FIG. 10 shows an example of wide field OPTIR data measured under the embodiment shown in FIG. 2. The sample was a cross-section of a multilayer polymer film. The sample was illuminated with probe light source comprising 7 W, 445 nm wavelength LED source in CW operation, focused onto the sample with a 40×0.78 NA Cassegrain objective. The sample was simultaneously illuminated with pulses of IR light from a QCL based source operating at 1293 cm$^{-1}$. Probe light reflected and scattered from the sample was collected with the same Cassegrain objective and directed towards a scientific CMOS camera with 1200× 1200 pixels. Five hundred frames were co-added with IR pulses on and IR pulse off. The sample chemical image 1000 is the difference between images with the IR laser on versus with the IR laser off. The chemical image 1000 shows a 400×400 pixel image, with a scale of 3.04 pixels/micron, thus corresponding to an image size of 131×131 microns. Thus it is possible under an embodiment shown to use a camera based sensor to measure a signal indicative of IR absorption at a plurality of locations on a sample comprising a measurement area greater than 100×100 microns.

The embodiments described herein are exemplary. Modifications, rearrangements, substitute processes, alternative elements, etc. may be made to these embodiments and still be encompassed within the teachings set forth herein. One or more of the steps, processes, or methods described herein may be carried out by one or more processing and/or digital devices, suitably programmed.

Depending on the embodiment, certain acts, events, or functions of any of the method steps described herein can be performed in a different sequence, can be added, merged, or left out altogether (e.g., not all described acts or events are necessary for the practice of the algorithm). Moreover, in certain embodiments, acts or events can be performed concurrently, rather than sequentially.

The various illustrative logical blocks, optical elements, control elements, and method steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or "means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices or methods illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

We claim:

1. An apparatus for microscopic analysis of a sample by simultaneously characterizing infrared absorption characteristics of a plurality of spatially resolved locations corresponding to a wide area of the sample, the apparatus comprising:
   an infrared light source configured to illuminate the wide area of the sample with a beam of infrared radiation;
   a reflective objective arranged to receive the beam of infrared radiation from the infrared light source and illuminate the wide area of the sample at a first side thereof;
   a probe light source configured to generate a beam of probe radiation;
   a refractive objective arranged to receive the beam of probe radiation and illuminate the wide area of the sample at a second side thereof
   a collector configured to collect as collected probe radiation at least a portion of probe radiation from each of the plurality of spatially resolved locations on the sample;
   at least one camera configured to detect at least a portion of the collected probe radiation to generate signals indicative of infrared absorption corresponding to each one of the plurality of spatially resolved locations.

2. The apparatus of claim 1 wherein the infrared radiation source is tunable to produce the infrared beam with a variable wavelength and wherein the signals indicative of infrared absorption of the sample are detected at a plurality of infrared wavelengths.

3. The apparatus of claim 2 wherein the signals indicative of infrared absorption at a plurality of infrared wavelengths comprise infrared absorption spectra.

4. The apparatus of claim 1 further comprising an image co-adder wherein the image co-adder sums multiple camera frames to construct a co-added image with a dynamic range of at least $10^4$.

5. The apparatus of claim 1 where the co-added image has a dynamic range of at least $10^5$.

6. The apparatus of claim 1 where the co-added image has a dynamic range of at least $10^6$.

7. The apparatus of claim 1 wherein the plurality of sample locations measured simultaneously comprise an area of at least 100 μm in diameter.

8. The apparatus of claim 1 further comprising a gate function that limits a duration of time over which the camera detects collected probe radiation from the plurality of sample locations.

9. The apparatus of claim 8 wherein the gate function limits at least one of: (a) an exposure time of the camera; and (b) a pulse duration length of the beam of probe radiation.

10. The apparatus of claim 1 wherein signals indicative of infrared absorption of the plurality of sample locations are generated by comparing a first set of camera frames collected with the infrared light source irradiating the sample and a second set of camera frames collected with the infrared light source not irradiating the sample.

11. The apparatus of claim 1 wherein the collector comprises an objective with a numerical aperture (NA) of at least 0.4.

12. The apparatus of claim 1 wherein the collector comprises an objective with a numerical aperture (NA) of at least 0.6.

13. The apparatus of claim 1 wherein the probe light source is an incoherent light source.

14. The apparatus of claim 1 wherein the probe light source comprises at least one light emitting diode.

15. The apparatus of claim 1 wherein generating signals indicative of infrared absorption corresponding to each one of the plurality of spatially resolved locations is based on measuring fluctuations in phase of the collected probe light caused by infrared absorption at the sample.

16. A method of operating a system for simultaneously characterizing infrared absorption characteristics of plurality of locations on a sample, the method comprising the steps of:
   illuminating the plurality of locations of the sample with a reflective objective and an infrared light source that are arranged to illuminate a first side of the sample;
   illuminating the plurality of locations of the sample with a refractive objective and a probe light source that are arranged to illuminate a second side of the sample;
   collecting probe radiation from the plurality of sample locations;
   detecting collected probe radiation with at least one camera; and
   analyzing camera detected probe radiation to generate signals indicative of infrared absorption of the plurality of locations on the sample.

17. The method of claim 16 further comprising tuning the infrared light source to produce the infrared beam having a variable wavelength and wherein the signals indicative of infrared absorption of the sample are detected at a plurality of infrared wavelengths.

18. The method of claim 16 wherein the signals indicative of infrared absorption comprise infrared absorption spectra.

19. The method of claim 18 wherein the infrared absorption spectra are measured at a rate exceeding 20 spectra per second.

20. The method of claim 18 wherein the infrared absorption spectra are measured at a rate exceeding 50 spectra per second.

21. The method of claim 18 wherein the infrared absorption spectra are measured at a rate exceeding 90 spectra per second.

22. The method of claim 16, wherein the system further comprises an image co-adder and the method further comprises, using the co-adder, combining multiple camera frames to construct a co-added image with a dynamic range of at least $10^4$.

23. The method of claim 22 wherein the co-added image has a dynamic range of at least $10^5$.

24. The method of claim 22 wherein the co-added image has a dynamic range of at least $10^6$.

25. The method of claim 16 further comprising simultaneously measuring an area of at least 100 µm in diameter.

26. The method of claim 16 further comprising applying a gate function to limit a duration of time over which the camera detects collected probe radiation from the plurality of sample locations.

27. The method of claim 26 wherein the gate function limits at least one of: (a) an exposure time of the camera; and (b) a pulse duration length of the beam of probe radiation.

28. The method of claim 16 wherein signals indicative of infrared absorption of the plurality of sample locations are generated by comparing a first set of camera frames collected with the infrared light source irradiating the sample and a second set of camera frames collected with the infrared light source not irradiating the sample.

29. The method of claim 16, wherein generating signals indicative of infrared absorption corresponding to each one of the plurality of spatially resolved locations is based on measuring fluctuations in phase of the collected probe light caused by infrared absorption at the sample.

* * * * *